United States Patent
Raddatz

(10) Patent No.: US 7,764,998 B1
(45) Date of Patent: Jul. 27, 2010

(54) IMPLANTABLE CARDIAC STIMULATION DEVICES WITH BACK-UP DEFIBRILLATION

(75) Inventor: Lindsey Raddatz, Toluca Lake, CA (US)

(73) Assignee: Pacesetter, Inc., Sylmar, CA (US)

( * ) Notice: Subject to any disclaimer, the term of this patent is extended or adjusted under 35 U.S.C. 154(b) by 580 days.

(21) Appl. No.: 11/567,151

(22) Filed: Dec. 5, 2006

(51) Int. Cl.
*A61N 1/39* (2006.01)
(52) U.S. Cl. .................................. 607/5; 607/7; 607/15
(58) Field of Classification Search ........................ None
See application file for complete search history.

(56) References Cited

U.S. PATENT DOCUMENTS

| 4,595,009 | A | | 6/1986 | Leinders | |
|---|---|---|---|---|---|
| 5,003,975 | A | * | 4/1991 | Hafelfinger et al. | 607/28 |
| 5,174,288 | A | | 12/1992 | Bardy et al. | |
| 5,222,492 | A | * | 6/1993 | Morgan et al. | 607/5 |
| 5,224,475 | A | * | 7/1993 | Berg et al. | 607/8 |
| 5,571,141 | A | | 11/1996 | McNeil et al. | |
| 5,879,374 | A | * | 3/1999 | Powers et al. | 607/5 |
| 6,161,040 | A | * | 12/2000 | Blunsden | 607/5 |
| 6,714,808 | B2 | * | 3/2004 | Klimberg et al. | 600/411 |
| 2005/0245970 | A1 | * | 11/2005 | Erickson et al. | 607/2 |

FOREIGN PATENT DOCUMENTS

WO 9209329 6/1992

* cited by examiner

*Primary Examiner*—Carl H Layno
*Assistant Examiner*—Paula J Stice

(57) ABSTRACT

Systems and methods are provided for providing back-up or redundant defibrillation in case of a faulty defibrillation path or faulty defibrillation circuit element. In case a problem is detected with one or more active or enabled electrode paths, the system and method selects available redundant circuits for active use.

11 Claims, 4 Drawing Sheets

IMPLANTABLE CARDIAC STIMULATION DEVICES WITH BACK-UP DEFIBRILLATION

BACKGROUND OF THE INVENTION

1. Field of the Invention

The invention relates to the field of implantable medical devices and in particular to systems and methods of preventing damage to output stage components of an implantable medical device and providing back-up or safe mode operation in case of a shorted output circuit.

2. Description of the Related Art

A variety of implantable medical devices are known to automatically monitor a patient's physiologic condition and to selectively provide therapy when indicated. Implantable cardioverter defibrillators (ICDs) and/or pacemakers are implantable medical devices which are configured to monitor a patient's cardiac activity and selectively provide therapy for a variety of potentially dangerous or life-threatening medical conditions such as cardiac arrhythmias and/or atrial or ventricular fibrillations. Implantable ICDs typically include a high voltage circuit for generating high voltage waveforms for delivery to patient tissue and a microprocessor-based controller which regulates the delivery of the high voltage waveform. The high voltage circuit and the controller circuitry are generally encased within a biocompatible can or housing along with a battery to power the device.

Implantable ICDs and/or pacemakers typically also include one or more implantable patient leads with associated electrodes. The patient leads include insulated conductors connected at one end to a corresponding electrode and at the other to the high voltage circuitry and controller in the can or housing. The patient leads are frequently configured for transvenous catheterization to place the electrodes into contact with the patient's cardiac tissue.

The leads also typically include relatively thin insulated conductors and are made to be at least partially flexible to accommodate passage through curved vein sections, as well as to accommodate internal movement within the veins and more particularly adjacent the beating heart. The thin nature of the conductors, as well as the constant exposure to vibration and physical movement due to the beating heart muscle as well as other patient movement, can result in lead abrasion or in some cases degradation of the insulation within the lead.

Degradations in the insulative material and lead abrasions tend to result in problematic conductive paths between the distal electrodes and the implantable device housing and in some cases may create a complete short circuit along the conductive path. If a short circuit is formed between one of the distal electrodes and the implantable device housing, the current of a defibrillation shock running through the path may be above the tolerance of some of the vital components of the implantable device and may thus result in irreparable damage to these components. These components generally include output stage transistors that generate the defibrillation waveform.

Damage to these transistors can result in inoperability of the device such that it is no longer able to provide therapy. Furthermore, subsequent charging of capacitors in the high voltage circuit can generate leakage currents that might get injected into the patient's tissue and in some instances induce a fibrillation arrhythmia.

In order to prevent induced arrhythmias, some implantable ICDs include a shorted output stage detection algorithm that monitors various components of the high voltage circuit and turns off the high voltage charging upon detecting a damaged component. This feature decreases the risks of induction. The shorted output stage detection algorithm, however, acts upon detection of a damage and does not assist in preventing the damage.

In order to prevent damage to the components, some implantable ICDs include a shorted output stage prevention algorithm that can detect a short circuit and turn off the high voltage function before the components are damaged. Thus, the shorted output stage prevention algorithm can help prevent damage to some vital components. However, because upon detection of a short circuit, the high voltage functions are aborted, the patient may be left without therapy for an unacceptable period of time. This may lead to injury especially in instance where if the patient was in fibrillation when the short circuit was detected.

SUMMARY OF THE INVENTION

From the foregoing, it will be appreciated that there is a need and desire for implantable medical device systems and methods of operating these systems to better accommodate unexpected faulty output stage paths. It would be desirable for such new systems and methods of operation to provide back-up or redundancies to maintain the ability to provide therapy in case of a faulty path.

These needs are satisfied by the invention which, in one embodiment, includes an implantable cardiac stimulation device for delivering electrical stimulation to the heart of a patient, the device comprising a plurality of leads adapted to be implanted adjacent the heart of the patient so as to be able to provide electrical stimulation to the heart of the patient and a controller adapted to be coupled with the leads, so as to induce the delivery of electrical stimulation to the heart of the patient via a first configuration of the leads, wherein the controller monitors a characteristic of performance of the leads and, when the controller determines that there is a potential current path of the therapeutic electrical stimulation that could result in damage to components of the controller, the controller inhibits the delivery of the electrical stimulation via the first configuration of the leads and re-configures the leads such that electrical stimulation is delivered via a second configuration of the leads.

Another embodiment of the invention includes an implantable cardiac stimulation device for delivering electrical stimulation to a heart of a patient, the device comprising a battery, a high voltage circuit that generates a high voltage output waveform adapted to be applied to the heart of the patient, a first, a second, and a third electrode adapted to be implanted adjacent the heart of the patient, wherein in a first configuration the first and the second electrodes are configured to receive and deliver the high voltage waveform to the heart of the patient, an overcurrent protection circuit adapted to monitor the current flowing through the first and the second electrodes during delivery of the high voltage waveform and adapted to inhibit the delivery of the high voltage waveform when the current reaches a level indicative of potential damage to one or more components along a path of the current, and a controller that controls the delivery of the high voltage waveform to the heart of the patient, wherein upon detection of a potential damage to one or more components of the current path, the controller is adapted to re-configure the electrodes to a second configuration such that either the first and the third or the second and the third electrode receive and deliver the high voltage waveform to the heart of the patient.

Yet, another embodiment includes a method of delivering electrical stimulation to the heart of a patient, the method comprising delivering electrical stimulation to the heart of the patient via a first configuration of one or more leads, monitoring a characteristic of performance of the leads, determining whether a faulty current path exists in the first configuration of the leads, inhibiting delivery of electrical stimulation via the first configuration of the leads if a faulty current path exists in the first configuration of the leads, and re-configuring the leads such that the electrical stimulation is delivered through a second configuration of one or more leads.

These and other objects and advantages of the invention will become more apparent from the following description taken in conjunction with the accompanying drawings.

DETAILED DESCRIPTION

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
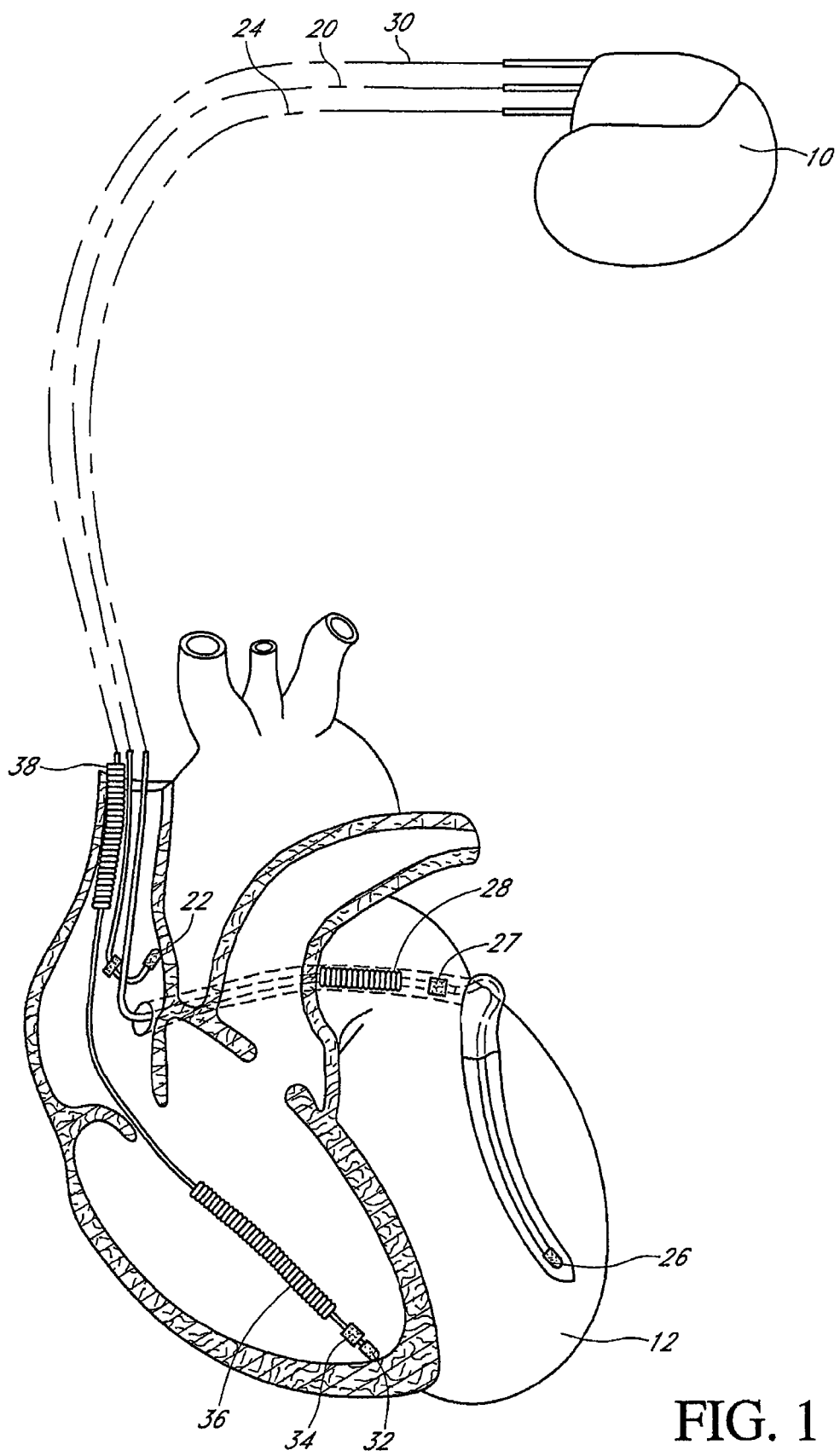
FIG. 1 is a simplified diagram illustrating a therapeutic appliance with an implantable stimulation device in electrical communication with at least three leads implanted into a patient's heart for delivering multi-chamber stimulation and shock therapy and a mechanical structural support to restrain excessive distension of the heart.

As shown in FIG. 1, there is a stimulation device 10 in electrical communication with a patient's heart 12 by way of three leads 20, 24 and 30, suitable for delivering multi-chamber stimulation and shock therapy. The stimulation device 10 is coupled to an implantable right atrial lead 20 which allows the device 10 to sense atrial cardiac signals, and to provide right atrial chamber stimulation therapy. The right atrial lead 20 has at least an atrial tip electrode 22 and a right atrial ring electrode 25. The atrial tip electrode 22 and right atrial ring electrode 25 are typically implanted in the patient's right atrial appendage, as shown.

The stimulation device 10 is coupled to a coronary sinus lead 24 which is designed for placement in the coronary sinus region via the coronary sinus ostium (OS). The coronary sinus lead 24 works with the simulation device 10 to sense left atrial and ventricular cardiac signals and provide left chamber pacing therapy. As used herein, the phrase coronary sinus region refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals. Additionally, the coronary sinus lead 24 is configured to deliver left ventricular pacing therapy using at least a left ventricular tip electrode 26, deliver left atrial pacing therapy using at least a left atrial ring electrode 27, and/or deliver shocking therapy using at least a left atrial coil electrode 28.

The stimulation device 10 is also in electrical communication with the patient's heart 12 by way of an implantable right ventricular lead 30. In one embodiment, the right ventricular lead 30 includes a right ventricular tip electrode 32, a right ventricular ring electrode 34, a right ventricular (RV) coil electrode 36, and an SVC coil electrode 38.

Typically, the right ventricular lead 30 is transvenously inserted into the heart 12 so as to place the right ventricular tip electrode 32 in the right ventricular apex. This causes the RV coil electrode to be positioned in the right ventricle and the SVC coil electrode 38 to be positioned in the superior vena cava. Accordingly, the right ventricular lead 30 is capable of receiving cardiac signals and delivering stimulation in the form of pacing and shock therapy to the right ventricle.

Figure 2:
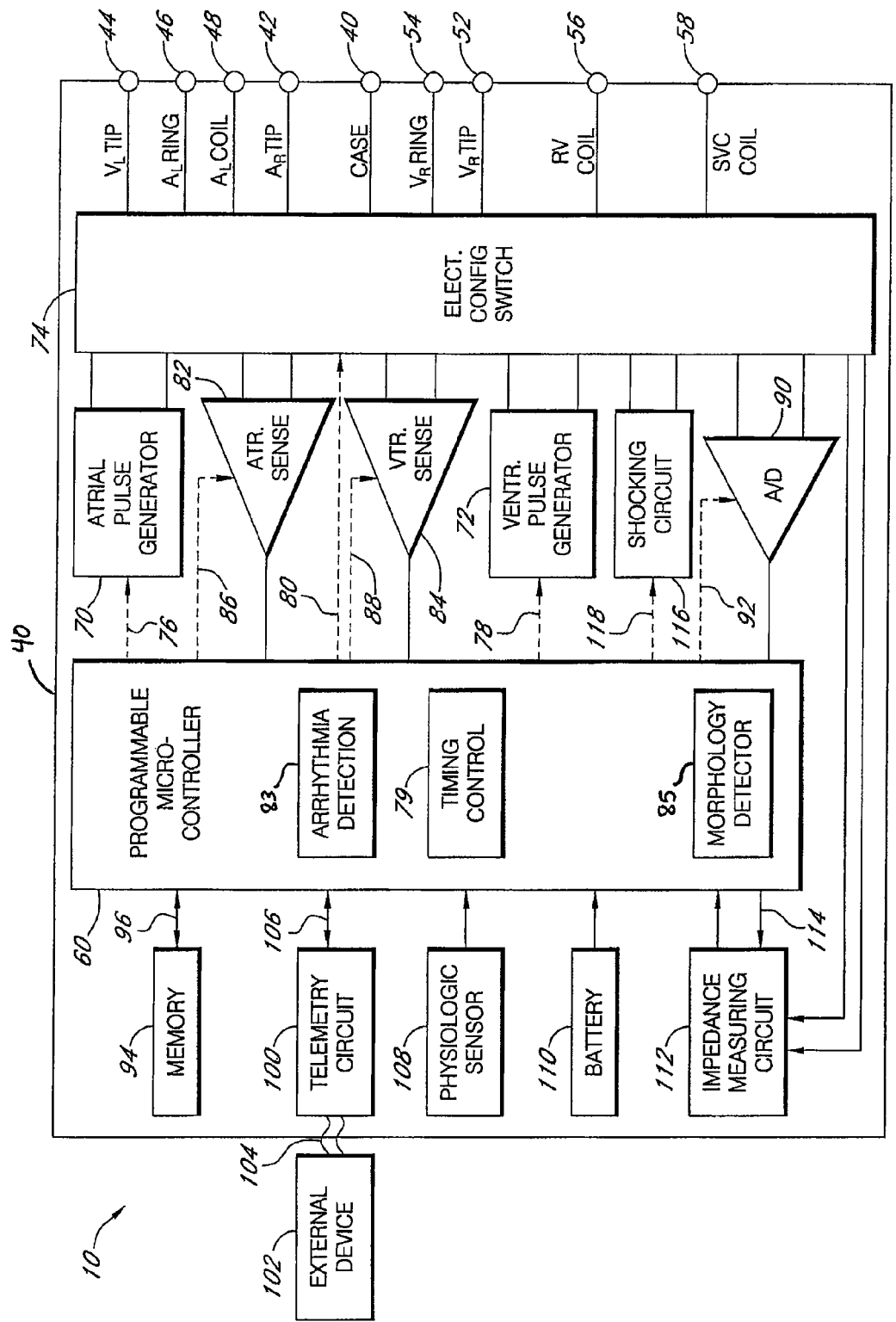
FIG. 2 is a functional block diagram of a multi-chamber implantable stimulation device of FIG. 1 illustrating the basic elements of a stimulation device which can provide cardioversion, defibrillation, and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the can, case, or case electrode and may be programmably selected to act as the return electrode for all unipolar modes. The housing 40 may further be used as a return electrode alone or in combination with one or more of the coil electrodes, 28, 36, and 38 for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). The connector includes at least a right atrial tip terminal ($A_R$ TIP) 42 adapted for connection to the atrial tip electrode 22 to achieve right atrial sensing and pacing.

The connector further includes at least a left ventricular tip terminal ($V_L$ TIP) 44, a left atrial ring terminal ($A_L$ RING) 46, and a left atrial shocking terminal ($A_L$ COIL) 48 to achieve left chamber sensing, pacing and shocking. The left ventricular tip terminal ($V_L$ TIP) 44, left atrial ring terminal ($A_L$ RING) 46, and left atrial shocking terminal ($A_L$ COIL) 48 are adapted for connection to the left ventricular ring electrode 26, the left atrial tip electrode 27, and the left atrial coil electrode 28, respectively.

The connector also includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58 to support right chamber sensing, pacing and shocking, The right ventricular ring terminal ($V_R$ RING) 54, right ventricular shocking terminal ($R_V$ COIL) 56, and SVC shocking terminal (SVC COIL) 58 are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The microcontroller 60 may also include various circuits and circuit components of the device 10 that are not shown as being included in the microcontroller 60 in FIG. 2. For example, the microcontroller 60 may include a memory 94, a shocking circuit 116, and an impedance measuring circuit 112. The microcontroller 60 either with or without the associated circuitry may also be referred to as a controller in this description. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the sensing polarity of the cardiac signal by selectively closing the appropriate switches, as is also known in the art. In this way, the clinician may program the sensing polarity independently of the stimulation polarity.

Each sensing circuit, 82 and 84, preferably employs one or more low power precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein sensing is reserved for the noting of an electrical signal, and detection is the processing of these sensed signals and noting the presence of an arrhythmia.

The timing intervals between sensed events (e.g., P-waves, R-waves, and depolarization signals associated with fibrillation) are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as tiered therapy).

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a rate-responsive sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. In addition to the physiological sensor 108, the microcontroller 60 includes a morphology detector 85 for detecting morphology of various heart ailments from the received signals.

The stimulation device additionally includes a battery 110 which provides operating power to all of the circuits shown in FIG. 2. For the stimulation device 10, which employs shocking therapy, the battery 110 is generally capable of operating at low current drains for long periods of time and capable of providing high-current pulses (for capacitor charging) when the patient requires a shock pulse. The battery 110 also generally has a predictable discharge characteristic so that elective replacement time can be detected. In one embodiment, the device 10 preferably employs at least one lithium/silver vanadium oxide battery. In another embodiment, the battery 110 will preferably be lithium iodide or carbon monoflouride or a hybrid of the two.

As further shown in FIG. 2, the device 10 has an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

In the case where the stimulation device 10 is intended to operate as an implantable cardioverter/defibrillator (ICD) device, it is generally configured to detect the occurrence of an arrhythmia, and automatically apply an appropriate electrical shock therapy to the heart aimed at terminating the detected arrhythmia. Thus, the microcontroller 60 further includes an arrhythmia detection circuit 83 for detecting arrhythmias.

Furthermore, the microcontroller 60 controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, which are selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (e.g., using the RV electrode as a common electrode). The electrodes that are used at a given point in time to apply the shocking pulse are referred to as active electrodes and the electrodes that are not used are referred to as inactive.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In order to generate and deliver the shocking pulses to the patient's heart, the active electrodes should generally be in good working conditions. However, because the electrodes and their insulative materials are generally very thin and because the electrodes are constantly exposed to vibrations and physical movements of the beating heart, breaks in the insulative material and/or abrasions in the leads are not uncommon. A break in the insulative material and/or abrasions in one or more of the leads 20, 24, or 30 may result in a problematic path or in some cases a complete short circuit between the two electrodes and the shocking circuit 116. When a short circuit is formed, the current of a shock running through the shocking circuit 116 may be above the tolerance of various components of the shocking circuit 116 and may thus result in substantial damage to those components. Thus, in order to prevent damage to these components, the shocking circuit 116 may include circuitry for overcurrent protection.

Figure 3:
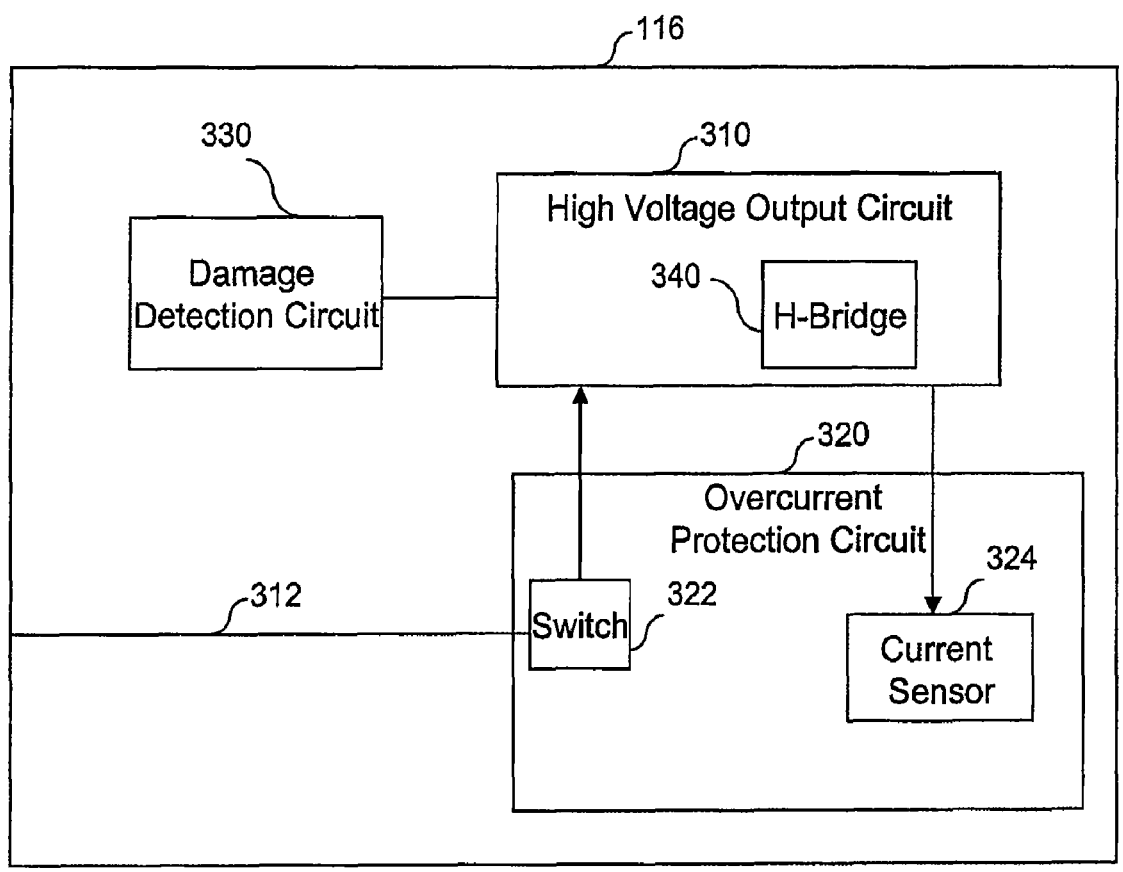
FIG. 3 is a functional block diagram of a shocking circuit having output stage damage detection and prevention circuitry.

FIG. 3 is a simplified block diagram of a shocking circuit 116 which includes an overcurrent protection circuit 320. As illustrated, the shocking circuit 116 includes a high voltage output circuit 310, an overcurrent protection circuit 320, and a damage detection circuit 330. The high voltage output circuit 310 generally receives energy from the battery 110 through a high voltage line 312 via a charging circuit (not shown) and a transformer (not shown) in a known manner and generates a high voltage shocking waveform. In one embodiment, the high voltage output circuit includes an H-bridge structure 340 which functions as an output switching device. The H-bridge structure, in one embodiment, includes four bipolar transistors. By sequentially switching the transistors, the H-bridge structure generates a high voltage biphasic waveform which is then applied to the patient's heart 12 via one or more active electrodes.

When the current of the high voltage waveform runs through a shorted circuit path, however, the energy may be above the tolerance of the transistors and may thus result in damage to these components. In order to prevent damage, the shocking circuit 116 includes an overcurrent protection circuit 320. The overcurrent protection circuit 320 monitors the current that flows through the high voltage output circuit 310 and turns off the high voltage output circuit 310, when the amount of current exceeds a predetermined threshold.

In one embodiment, the overcurrent protection circuit 320 includes a switch 322 and a current sensor 324. The switch 322 is connected in between the high voltage output circuit 310 and the high voltage line 312. The current sensor 324 is disposed such that the current that flows across the high voltage output circuit 310 and the active electrodes also passes through the current sensor 324. When the current exceeds a predetermined threshold, the current sensor 332 turns off the switch 322 such that the high voltage output circuit 310 is turned off. This is advantageous because it prevents the current from flowing through the transistors of the high voltage output circuit 310 and thus from damaging those transistors.

Other methods of detecting faulty paths are also possible. For example, in one embodiment, the device may utilize the impedance measuring circuit 112 of FIG. 1 to measure impedance across the active electrodes to determine whether a short circuit exists. This impedance measurement may be performed periodically. For example, in one embodiment, impedance may be measured one or more times a day. Other configurations are also possible. For example, in some embodiments, capacitance may also be measured.

In circumstances where it is critical to apply a high voltage waveform to terminate a life-threatening arrhythmia or fibrillation, turning off the high voltage output circuit 310 and leaving the patient without defibrillation might be dangerous. Thus, a system and method of providing back-up defibrillation is also provided.

Accordingly, in one embodiment, upon detecting a faulty path, one or more of the active electrodes are switched with one or more of the inactive electrodes to attempt to perform the life-saving defibrillation through a path that does not contain a shorted circuit. For example, if the stimulation device 10 was programmed to apply the defibrillation shock through the RV coil electrode 36 and the SVC coil electrode 38 (see, FIG. 1) and the overcurrent protection circuit 320 detected that the current flowing through that path exceeds a predetermined threshold, the configuration is changed to apply the shock through different electrodes such as the RV coil electrode 36 and the housing 40.

Other configurations are also possible. For example, in one embodiment, if the stimulation device 10 was programmed to apply the defibrillation shock through the RV coil electrode 36 and the housing 40 and the overcurrent protection circuit 320 detected that the current flowing through that path exceeds the predetermined threshold, the configuration is changed to apply the shock through the RV coil electrode 36 and the SVC coil electrode 38.

Generally, when an implantable medical device is initially configured with a particular configuration of active electrodes, the device is also programmed with a particular set of stimulation waveform parameters that are suitable for the patient at that configuration. These parameters include, for example, proper timing and energy level of the stimulation waveforms. When, the configuration of active electrodes is changed, stimulation waveform parameters for the new configuration are generally not available. Thus, in one embodiment, the stimulation waveforms are delivered using the waveform parameters programmed for the previous configuration of electrodes.

However, the waveform parameters programmed for the previous configuration may not generate stimulation waveforms having enough energy to overcome arrhythmias and/or fibrillations in the new configuration. Thus, in one embodiment, the stimulation waveforms generated by the new configuration are delivered at maximum energy to ensure that the waveforms can overcome arrhythmias and/or fibrillations.

In another embodiment, the implantable medical device is preprogrammed with a particular set of waveform parameters for each possible electrode configuration. In this embodiment, when electrode configuration is changed to a new configuration, a microcontroller changes the stimulation parameters to those stored in memory for the new configuration. In yet another embodiment, previous trends and/or sensed data is examined to determine stimulation waveform parameters that are appropriate for the new configuration.

When the transistors are damaged before the high voltage output circuit 310 is turned off, in case of a short circuit, or transistors and/or other components of the output circuit 310 are damaged for reasons other than existence of a short circuit, continuing to charge the circuit 310 may result in generating leakage current which can be injected into the patient's tissue and in some cases cause an induction by inducing a fibrillation arrhythmia. In order to prevent such induction, the high voltage output circuit 310 includes a damage detection circuit 330 that monitors for and detects damage to the transistors and/or other components of the high voltage output circuit 310 and turns off all high voltage functions once damage to a vital component is detected. Generally, the damage detection circuit 330 monitors for leakage current over a low voltage range at the beginning of a therapy to assure that the amount of current flowing through the circuit is low enough to not induce fibrillation in the patient.

In one embodiment, the damage detection circuit 330 monitors the amount of charge across the positive and negative terminals of certain output capacitors for a particular period of time to determine whether the capacitors' charge reaches a pre-determined voltage. If the capacitors' charge does not reach the pre-determined voltage in the allotted time, then it is determined that one or more of the output transistors are damaged. This is because current leakage through one or more pairs of damaged transistors between the positive and negative terminals of a capacitor drains the voltage off of the capacitor as fast as charging takes place. As a result, the capacitors generally do not maintain charge when the output transistors are damaged.

Figure 4:
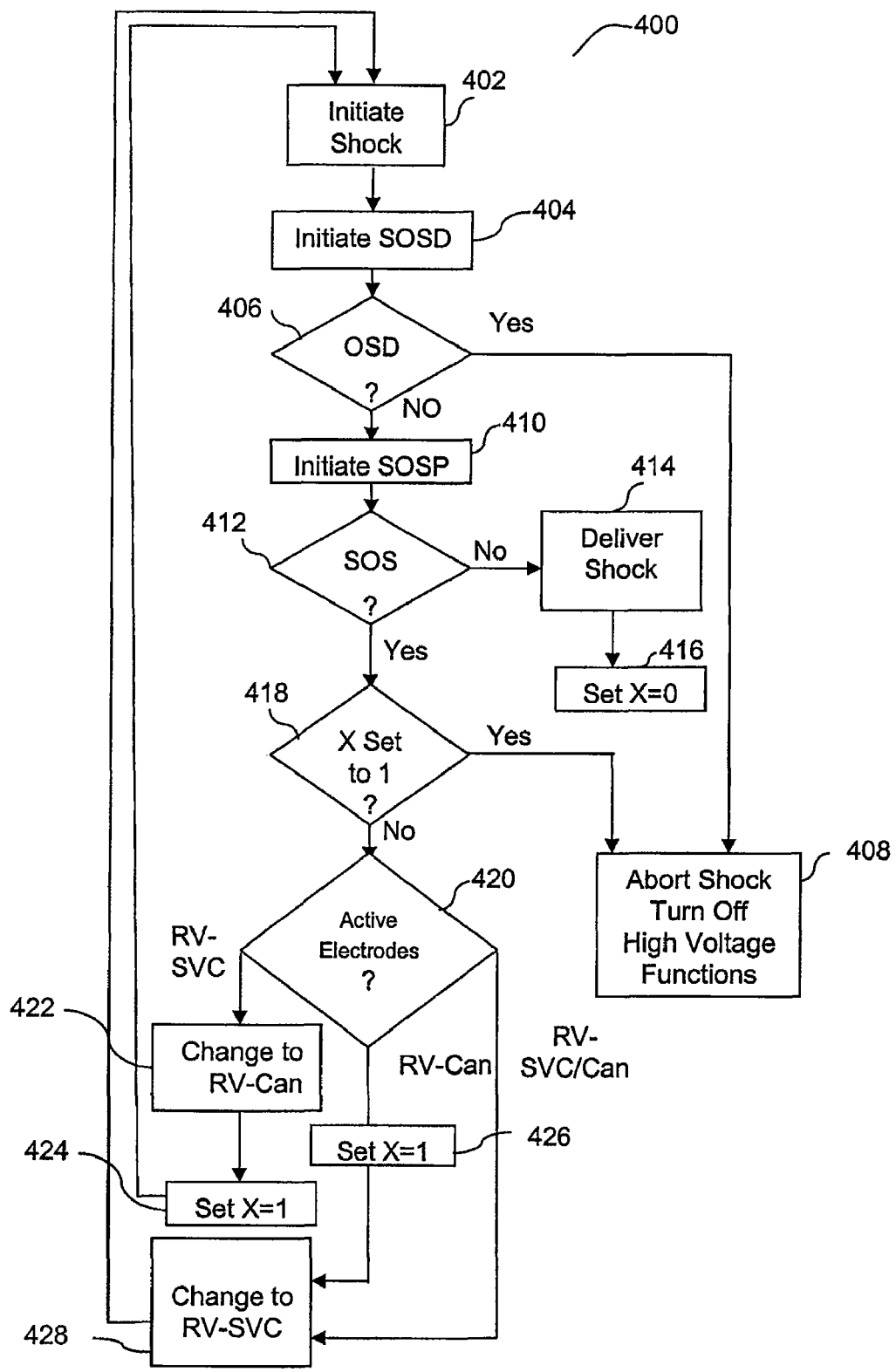
FIG. 4 is a flow-chart of one embodiment of a method of providing back-up modes of operation in an implantable medical device in case of circuit problems.

In FIG. 4, a flow chart is shown describing an overview of the operation and novel features implemented in embodiments of the device 10. In this flow chart, the various algorithmic steps are summarized in individual exemplary blocks. Such exemplary blocks describe specific actions or decisions that are made or carried out as the algorithm proceeds. Where a microcontroller (or equivalent) is employed, the flow charts presented herein provide the basis for a control program that may be used by such a microcontroller (or equivalent) to effectuate the desired control of the stimulation device 10. Those skilled in the art may readily write such a control program based on the flow charts and other descriptions presented herein. It will be understood that the steps, processes, and components of the method 400 would generally proceed in parallel with the other operations and processes of the device 10 as previously described.

The method 400 begins in a step 402 where a high voltage shock is initiated. This occurs, in one embodiment, when a microcontroller of an implantable stimulation device determines that a fibrillation has occurred and sends a signal to a shocking circuit to trigger a defibrillation shock. Upon receiving the signal from the microcontroller, the shocking circuit generates a waveform to be applied to a patient's heart through one or more active electrodes, such as the electrodes disclosed herein. After the shocking waveform is generated and a shock is thus initiated, the method 400 proceeds to a step 404 where a shorted output stage detection (SOSD) algorithm is triggered.

The SOSD algorithm may be implemented using a circuit element such as the damage detection circuit disclosed herein to examine specific components of a high voltage output circuit and determine if any of the components have been damaged. If damage to one or more vital components is detected at step 406, the method 400 proceeds to a step 408 to abort the shock and turn off the high voltage functions of the high voltage output circuit. This is done to avoid further charging of the damaged circuit and to prevent current leakage and potential induction and fibrillation.

If no damage is detected at step 406, then the method 400 proceeds to a step 410 to trigger a shorted output stage prevention (SOSP) algorithm. The SOSP algorithm is configured to detect potential shorted output paths and thus help prevent damage to various circuit components of the high voltage output circuit. The SOSP algorithm may be implemented using circuit elements such as the overcurrent prevention circuit disclosed herein.

Alternatively, means other than overcurrent detection may be used to check for faulty leads. For example, a controller may be programmed to periodically perform lead integrity measurements and to set up flags in memory when the integrity measurements indicate that a lead may be faulty. The SOSP algorithm may be configured to look in memory for flags that indicate the current lead configuration includes a faulty lead.

Referring back to FIG. 4, at step 412, the method 400 determines If a shorted output path or a damaged lead has been detected by the SOSP algorithm. If a shorted output path or a damaged lead has not been detected, then the method 400 proceeds to step 414 to deliver the shock in a known manner. The method 400 consequently proceeds to a step 416 to set a flag X to zero.

The flag X is utilized to determine the number of times the method 400 has been consecutively implemented. This information is used to determine the appropriate backup configuration and to determine whether or not the method should continue switching the configurations or it should abort the high voltage functions.

If a shorted output path or a damaged lead is detected at step 412, the method 400 proceeds to step 418 to determine whether the flag X has been set to one. If it is determined that the flag X has been set to one, then the method 400 proceeds to step 408 to abort the shock and turn off all high voltage functions. However, if it is determined at step 418 that the flag X not been set to one, the method 400 then proceeds to step 420 to determine what electrodes are used as the active electrodes to apply the shock.

If the active electrodes are an RV and an SVC electrode, then the method 400 assumes that the faulty path is between the RV electrode and the SVC electrode and will thus proceed to step 422 to change the configuration. The method 400 will change the configuration to remove the SVC electrode from the path and will thus switch to a configuration using an RV electrode and a can, such as the can 40 disclosed herein. The method 400 then proceeds to step 424 to set the flag X to one. Setting the flag X to one creates an indication that all available configurations have been tested and if the current configuration is still problematic, shock should be aborted.

The method 400 then proceeds to step 426 to adjust the parameters of the shocking waveform. The parameters of the high voltage waveform are generally adjusted each time the configuration is changed. The parameters are adjusted because parameters used for the previous configuration may not be suitable for the new configuration. Thus, at step 426, the method 400 determines appropriate parameters for the new configuration and applies those parameters.

The method 400 then returns from step 426 to step 402 to initiate the shock through the new configuration. If an output stage damage or a shorted output stage path is again detected, this time the method 400 proceeds to step 408 to abort the shock and turn off the high voltage functions.

Referring back to step 420, If it is determined that the active electrodes are an RV electrode and a can, then the method 400 proceeds to step 428 to set the flag X to one. The method 400 then proceeds to step 430 to change the configuration. This time, assuming that the faulty path is between the can and a lead, the method 400 changes the configuration to remove the can from the path and instead use an RV electrode and an SVC electrode.

The method 400 then proceeds to step 426 to adjust the shocking waveform parameters and then returns to step 402 to attempt to apply the shock through this new configuration. If the new configuration is again found to be problematic, the method 400 this time proceeds to step 408 to abort the shock and turn off the high voltage functions.

If at step 420 it is determined the configuration is set for applying the shock through an RV electrode and a combination of an SVC electrode and a can, then the method 400 first assumes that the faulty path is between the can and a lead. This assumption is made because generally problems are more likely to occur in the can to lead path than the other available paths. Thus, the method 400 proceeds to step 430 to change the configuration such that an RV and an SVC electrode is used.

The method 400 then adjusts the waveform parameters at step 426 and then returns to step 402 to attempt to trigger and deliver the shock, as before. If the new configuration is again found to be problematic, because the flag X has not been set to one, the method 400 this time proceeds to step 420 to change the configuration again. Because the current active electrodes are the RV and SVC electrodes, the method 400 proceeds to step 422 to change the configuration to an RV electrode and a can and further proceeds to steps 424 and 426 to set the flag X to one and to adjust the waveform parameters.

Thus, if a faulty path is again detected when the method 400 returns to step 402 and attempts to trigger and deliver the shock, the method 400 proceeds to step 408 to abort the shock and turn off the high voltage functions.

Thus the method 400 provides redundant or back-up lead configurations which can be employed as needed should initial or primary active lead circuit paths experience problem or damage. The method 400 provides the ability to identify faulty circuit paths before these faulty paths cause any damage to circuit components. The method 400 further provides the ability to continue to provide therapy delivery via a backup lead configuration that does not include the faulty circuit path. Thus, the method 400 provides the ability to continue to provide live-saving therapy when one or more components or circuits of an implantable medical device experience problem or damage.

The method 400 also provides the ability to monitor various high voltage circuit components and to detect potential problems or damages to these components. The method 400 further provides the ability to turn off problematic circuit components and/or paths and to thus prevent unnecessary induction and injection of current into a patient's tissue.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device for delivering electrical stimulation to the heart of a patient, the device comprising:

a plurality of leads adapted to be implanted adjacent the heart of the patient so as to be able to provide electrical stimulation to the heart of the patient;

a high voltage circuit that generates a high voltage output waveform adapted to be applied to the heart of the patient;

a current sensor configured to monitor the amount of current flowing through the leads and the high voltage circuit, wherein the current sensor is adapted to determine if the amount of current exceeds a predetermined threshold; and a controller adapted to control delivery of the high voltage waveform so as to induce the delivery of electrical stimulation to the heart of the patient via a first configuration of the leads, wherein the controller is adapted to terminate the delivery of the electrical stimulation via the first configuration of the leads and to reconfigure the leads such that electrical stimulation is delivered via a second configuration of the leads when the amount of current flowing through the first lead configuration exceeds a predetermined threshold which is indicative of potential damage to one or more components along the path of the current.

2. The implantable cardiac stimulation device of claim 1, wherein the first configuration of the leads comprises an RV-coil electrode and an SVC-coil electrode and the second configuration of the leads comprises an RV-coil electrode and the housing of the implantable cardiac stimulation device.

3. The implantable cardiac stimulation device of claim 1, wherein the first configuration of the leads comprises an RV-coil and the housing of the implantable cardiac stimulation device and the second configuration of the leads comprises an RV-coil electrode and an SVC-coil electrode.

4. The implantable cardiac stimulation device of claim 1, wherein one or more treatment parameters of the electrical stimulation delivered via the second configuration are changed.

5. The implantable cardiac stimulation device of claim 4, wherein the one or more treatment parameters of the electrical stimulation are changed such that the electrical stimulation is delivered at maximum energy.

6. The implantable cardiac stimulation device of claim 1, wherein the electrical stimulation comprises high voltage defibrillation waveforms.

7. An implantable cardiac stimulation device for delivering electrical stimulation to a heart of a patient, the device comprising:
   a battery;
   a high voltage circuit that generates a high voltage output waveform adapted to be applied to the heart of the patient;
   a first, a second, and a third electrode adapted to be implanted adjacent the heart of the patient, wherein in a first configuration the first and the second electrodes are configured to receive and deliver the high voltage waveform to the heart of the patient;
   an overcurrent protection circuit adapted to monitor the current flowing through the high voltage circuit and the first and second electrodes during delivery of the high voltage waveform and adapted to terminate the deliver of the high voltage waveform when the current reaches a level indicative of potential damage to one or more components along a path of the current; and
   a controller that controls the delivery of the high voltage waveform to the heart of the patient;
   wherein upon detection of a potential damage to one or more components of the current path, the controller is adapted to re-configured the electrodes to a second configuration such that either the first and the third or the second and the third electrode receive and deliver the high voltage waveform to the heart of the patient.

8. The device of claim 7, wherein the overcurrent protection circuit comprises a current sensor that senses the current flowing through the electrodes and a switch coupled to the current sensor adapted to be activated when the current sensor senses a current that exceeds a predetermined threshold thereby creating an open circuit and preventing further current flow from the high voltage circuit.

9. The device of claim 7, wherein the first electrode comprises an RV-coil electrode, the second electrode comprises an SVC-coil electrode, and the third electrode comprises a housing of the implantable cardiac stimulation device.

10. The implantable cardiac stimulation device of claim 7, wherein one or more treatment parameters of the high voltage waveform delivered via the second configuration are changed.

11. A method of delivering electrical stimulation to the heart of a patient, the method comprising:
   detecting an arrhythmia using an implantable device;
   determining whether a high voltage output section of the implantable device has a shorted output stage;
   delivering electrical stimulation to the heart of the patient via a first configuration of one or more leads in response to the detection of an arrhythmia and a failure to detect a shorted output stage;
   monitoring a characteristic of performance of the leads;
   determining whether a faulty current path exists in the first configuration of the leads as a function of the measured current;
   terminating delivery of the electrical stimulation via the first configuration of the leads if a faulty current path exists in the first configuration of the leads; and
   re-configuring the leads such that the electrical stimulation is delivered through a second configuration of one or more leads.

* * * * *